(12) United States Patent
Kitajima

(10) Patent No.: US 7,443,579 B2
(45) Date of Patent: Oct. 28, 2008

(54) OPHTHALMIC MICROSCOPE

(75) Inventor: Nobuaki Kitajima, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 29 days.

(21) Appl. No.: 11/532,616

(22) Filed: Sep. 18, 2006

(65) Prior Publication Data

US 2007/0076294 A1    Apr. 5, 2007

(30) Foreign Application Priority Data

Sep. 30, 2005    (JP)    ............................. 2005-288231

(51) Int. Cl.
*G02B 21/06* (2006.01)
*G02B 21/00* (2006.01)

(52) U.S. Cl. .................. 359/388; 359/368; 359/385

(58) Field of Classification Search ......... 359/368–390, 359/885–892
See application file for complete search history.

(56) References Cited

U.S. PATENT DOCUMENTS 5,022,744 A * 6/1991 Leiter ........................ 359/385

7,027,238 B2 * 4/2006 Weiss ......................... 359/888
2001/0028441 A1 * 10/2001 Okamoto et al. ............ 351/214

FOREIGN PATENT DOCUMENTS

| JP | 2001-275978 | 10/2001 |
|----|-------------|---------|
| JP | 2004-139002 | 5/2004  |

\* cited by examiner

*Primary Examiner*—Thong Nguyen
(74) *Attorney, Agent, or Firm*—Edwards, Angel, Palmer & Dodge, LLP

(57) ABSTRACT

An ophthalmic microscope including an objective lens placed in face of an inspecting eye; a light source for radiating an illumination light, an illumination optics for directing the illumination light to the inspecting eye via the objective lens, an observation optics placed along with an optical axis of the objective lens, a lighting angle switch placed on a light path of the illumination light for changing the angle of incidence of the illumination light to the inspecting eye, and a correlated color temperature changer working in conjunction with the switching of the angle of incidence by the lighting angle switch to change the correlated color temperature of the illumination light.

25 Claims, 11 Drawing Sheets

Direction of radiation of the illumination light

| Light source | Degree | Presence or absence of a correlated color temperature changing filter | Inclination (°) |
|---|---|---|---|
| Halogen light source | Common cataracts | (1) Not required | (2) 2 |
| | Hypermature cataracts | (3) Required [3000K⇒6000K] | (4) 6 |
| Xenon light source | Common cataracts | (5) Required [6000K⇒3000K] | (6) 2 |
| | Hypermature cataracts | (7) Not required | (8) 6 |

Note: The numbers in parenthesis indicate the item numbers.

OPHTHALMIC MICROSCOPE

BACKGROUND OF THE INVENTION

1. Field of the Invention

The present invention relates to an ophthalmic microscope.

2. Description of the Related Art

Various ophthalmic operations have been conventionally performed. In particular, cataract surgery is one example of an ophthalmic operation that has been typically performed. "Cataracts" is an ophthalmic disease, wherein the natural lens of the eye becomes clouded due to aging or other causes, leading to decreased visual performance. A procedure called phacoemulsification (hereinafter, referred to as "the suction method") has been a commonly performed operation for cataracts. In the suction method, an incision is made along the edge of the cornea and the capsule, an aspirator is inserted into the incision to remove the clouded lens, and an intraocular lens (IOL) is implanted in place of the removed lens.

In the suction method, a surgical microscope is used to obtain an enlarged image of the patient's eye (hereinafter, referred to as "the operating eye"). In this case, transillumination (red reflex) has been widely utilized as one way of improving the visibility of the image. Transillumination is generated by diffusing the illumination of the surgical microscope and reflecting it onto the ocular fundus of the operating eye. In particular, this is extremely effective for confirming the location of the incision in the capsule in order to insert the aspirator, or for determining whether the clouded lens has been completely aspirated.

Various means have been conventionally proposed and implemented in order to obtain a preferred red reflex for the conductor of the surgery (hereinafter, referred to as "the operator"). A major example of such means includes "0° lighting" wherein a deflection mirror is placed between the right and left observation optical axis visible through a binocular surgical microscope in order to direct the illumination light to the operating eye along the optical axis of the objective lens, or a complete coaxial lighting wherein the optical axis of the illumination system (hereinafter, referred to as "the optical axis of the illumination light") is directed by a half mirror along the optical axis of the observation system (hereinafter, referred to as "observation optical axis").

However, in the case of 0° lighting, since the red reflex in the observation beam varies from right to left, there are problems in that, for example, the image is not favorably fused when viewing with binocular vision. In complete coaxis lighting, only a completely darkened image is obtained due to reduced amount of the observation light reflected by the half mirror. Thus, there is a problem of reduced visibility.

Therefore, a means called "angle lighting (slant lighting)" for illuminating at a certain angle to the observation optical axis has been widely employed. Conventional surgical microscopes employing angle lighting include, for example, that disclosed in Patent laid-open No. 2004-139002. Such a surgical microscope acts such that a partial area of the image where a red reflex cannot be obtained from a portion of the illumination light directed by one of paired deflection members is complemented by a red reflex obtained from the other portion of the illumination light directed by the other deflection member. Accordingly, a red reflex can be obtained across a wide range of the observable retina. In addition, a bright red reflex can be obtained by directing the illumination light to the operating eye simultaneously by a pair of deflection members.

Furthermore, an entity microscope is provided for conducting meticulous observation or photographing of the observation object, the patient's eye (hereinafter, referred to as "the inspecting eye"). For example, the microscope disclosed in Patent laid-open No. 2001-275978 is a known entity microscope that enables observation of the anterior and interior (the fundus) of the inspecting eye by inserting and removing the entity angle adjustment part on the right and left optical axis to change the entity angle. Such an entity microscope enables optimal observation and photographing or the like of the anterior, or fundus, of the inspecting eye promptly and easily by equipping the entity angle adjustment unit and the color temperature conversion element in order to transform the entity angle using the entity angle transformation unit depending on the observation of the anterior fundus of the eye, as well as to convert the correlated color temperature (the observed color (herein, "the color of the illumination light") of the blackbody temperature, that is, the numeric indication of color).

However, as in the case of cataracts, when the degree of cloudiness (intensity of the reflected light) varies depending on the progression of the condition where cloudiness spreads over the lens, for example, in the case of hypermature cataracts, a red reflex cannot be obtained even with complete coaxis lighting. It is extremely difficult to perform CCC (Continuous Circular Capsulorrhoxis, i.e. incision of the capsule) without a red reflex. When performing CCC for cases of hypermature cataracts, a method has been employed for observing the light reflected from the capsule of the lens using angle lighting and a red reflex obtained by the complete coaxis lighting. However, since the capsule of the lens has extremely high transparency and low reflection intensity, it is difficult to obtain sufficient visibility. Consequently, utilizing the ability of the eyeball tissue to transmit long wavelength light favorably and to reflect short wavelength light relatively, a light source containing xenon light (hereinafter, referred to as "xenon light") has been used. The xenon light features a correlated color temperature of approximately 6,000K, which is higher than that of the common halogen light source of microscopes.

On the other hand, for common cataract cases in which the condition has not progressed to this extent, that is, the lens has not clouded to such a degree (hereinafter, referred to as "common cataracts"), CCC can be effectively performed in the presence of a red reflex. However, in order to obtain a red reflex, an illumination light with a correlated color temperature of approximately 3,000K is required. Therefore, defects occur in microscopes employing a xenon light source.

As such, an ophthalmic microscope with complete coaxis lighting and angle lighting may have to be used depending on the medical condition, such as in the case of cataracts. Considering the purchase and maintenance cost of the device and the requirements for storage space, one device with multiple functions has been desired.

In addition, it is considered possible to prevent the above-mentioned problems by equipping the invention disclosed in Patent laid-open No. 2004-139002 with the invention disclosed in Patent laid-open No. 2001-275978, that is, equipping the conventionally existing filter mechanism with a correlated color temperature changing filter in order to change the correlated color temperature of the light source. However, it is difficult to say that the above problems can be completely prevented, since a changing operation or the like is still required. Furthermore, in order to reduce the burden on the operator or the conductor of the examination (hereinafter, referred to as "the examiner") having to perform the operation over long periods of time or conducting examinations many times, such as in mass screenings, it is necessary to develop an ophthalmic microscope that enables the examiner to change the observation conditions with a simple adjustment.

Consequently, the present invention has been developed in consideration of such circumstances. The invention intends to provide an ophthalmic microscope that includes complete coaxis lighting and angle lighting to allow the observation conditions and the correlated color temperature to be changed easily and promptly.

SUMMARY OF THE INVENTION

The present invention includes: an objective lens placed in front of an inspecting eye; a light source for radiating an illumination light; illumination optics for directing the illumination light to the inspecting eye via the objective lens; observation optics placed along an optical axis of the objective lens; a lighting angle switching device placed on a light path of the illumination light to change the angle of incidence of the illumination light directed on the inspecting eye to the optical axis of the objective lens; and a correlated color temperature changing device operating in conjunction with the switching of the angle of incidence by the lighting angle switching device to change the correlated color temperature of the illumination light.

EFFECT OF THE INVENTION

According to the characteristics of the present invention, since the correlated color temperature changing means enables the changing of the correlated color temperature of the illumination light, operating in conjunction with the switching of the injection angle of the illumination light, the correlated color temperature of the light source can be readily changed while simultaneously changing the injection angle of the illumination light. Therefore, it becomes possible to set the observation conditions according to the medical condition of the inspecting eye and expand the observation range of the inspecting eye. In addition, since the microscope is multi-functional, reduction of the price is not necessary and excessive storage space is not required, allowing the device to be used in hospitals with limited space or the like.

BRIEF DESCRIPTION OF THE DRAWINGS

In the accompanying drawings:

FIG. 3A is a front view of said closure plate and said correlated color temperature changing filter using a halogen light source. FIG. 3B is a side view of said closure plate and said correlated color temperature changing filter.

DETAILED DESCRIPTION OF THE REFERENCE EMBODIMENTS

Embodiments of the present invention will be explained in detail with reference to the following drawings. Unless otherwise noted, the ophthalmic microscope of the below embodiments is equipped with a halogen light source for the sake of simplicity. The ophthalmic microscope of Embodiment 2 is equipped with a xenon light source in place of a halogen light source.

Embodiment 1

(Structure of Each Component and the Entirety of the Ophthalmic Microscope)

Embodiment 1 of the present invention is an ophthalmic microscope equipped with a filter, which is a component of the correlated color temperature changing means, for changing the correlated color temperature, wherein the correlated color temperature changing means and the lighting angle switching means are constituted together by employing a closure plate containing a transparent piece that is a component of the lighting angle switching means.

Figure 1:
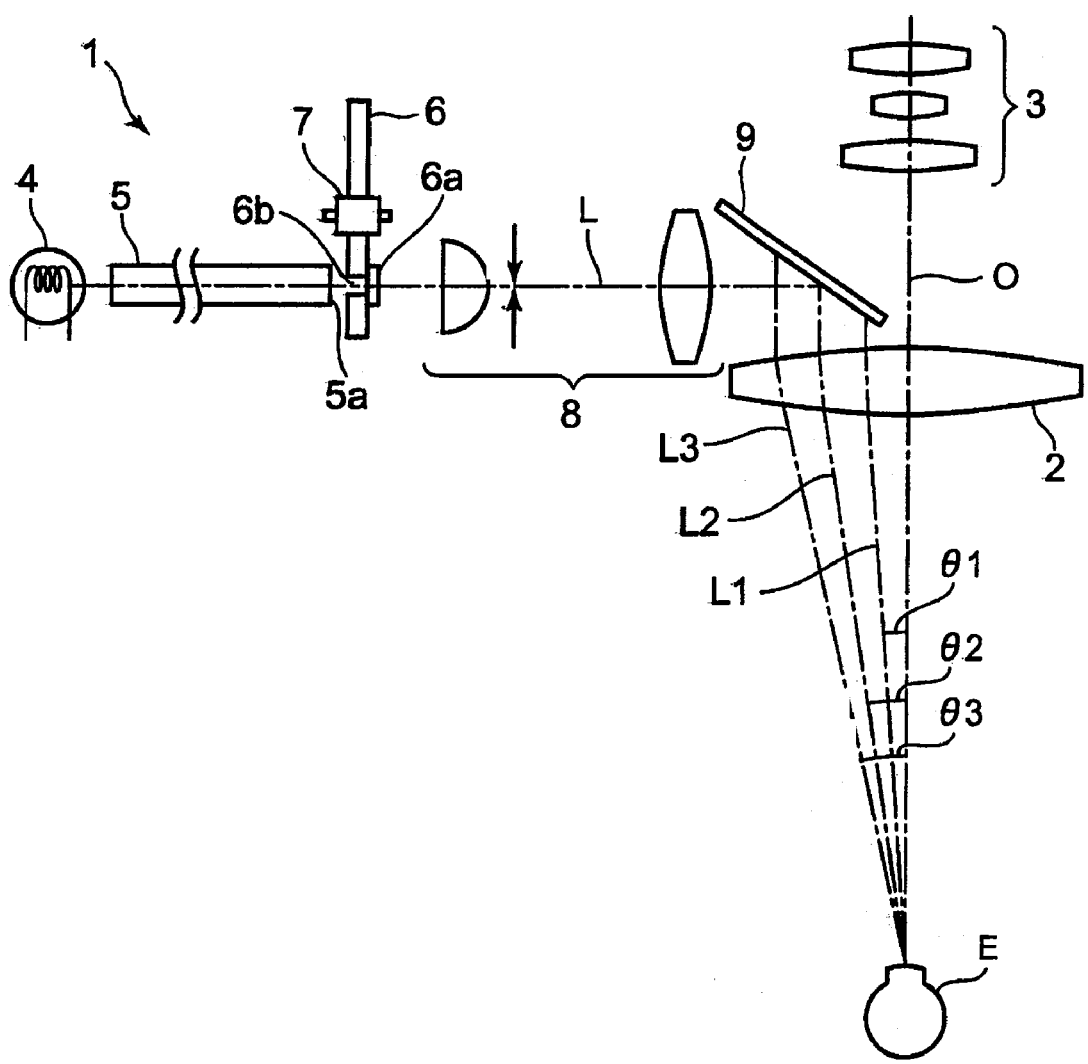
FIG. 1 is a block outline diagram showing the ophthalmic microscope in Embodiment 1 of the present invention.

FIG. 1 shows an outlined structure of the ophthalmic microscope 1 in the embodiment of the present invention. The ophthalmic microscope 1 enables observation through binocular vision. For example, it is placed on the objective lens 2 opposite to the inspecting eye E and the extension of the optical axis of the objective lens 2. The ophthalmic microscope 1 is equipped with an ocular lens component comprising an ocular lens for the left and right eyes (not shown), observation optics 3 including a lens group including a variable power lens or the like placed along the optical axis of the objective lens 2 to guide an observation light beam to the ocular lens, a light guide 5 including of an optical fiber bundle for guiding the illumination light from the light source 4, and a transparent piece 6b placed adjacent to the beam end 5a of this light guide 5 to selectively transmit a portion of the illumination light radiating from the beam end 5a.

Furthermore, the ophthalmic microscope is constituted to contain a closure plate 6 with a transparent piece 6b and a correlated color temperature changing filter 6a for changing the correlated color temperature of the illumination light from the light source 4 placed so as to cover the transparent piece 6b, a driving mechanism 7 for driving the rotation, illumination optics 8 including a lens group for guiding portion of the illumination light passed through the closure plate 6 to the area of the optical axis (hereinafter, referred to as "the observation optical axis") O of the observation optics 3, and a deflection mirror 9 located near the upper side of the objective lens 2 to reflect the illumination light, which was directed to the area of the observation optical axis O by the illumination optics 8, in order to change the direction and guide the light to the inspecting eye E via the objective lens 2. Meanwhile, the optical axis of the illumination light L is the optical axis of the illumination optics 8. It is constituted such that only a portion of the illumination light from the light source selectively transmitted by the transparent piece 6 on the closure plate 6 is directed to illuminate the inspecting eye E. However, hereinafter, for the sake of simplicity, the "portion of the illumination light" passed through the transparent piece 6b is simply described as the "illumination light".

Figure 2:
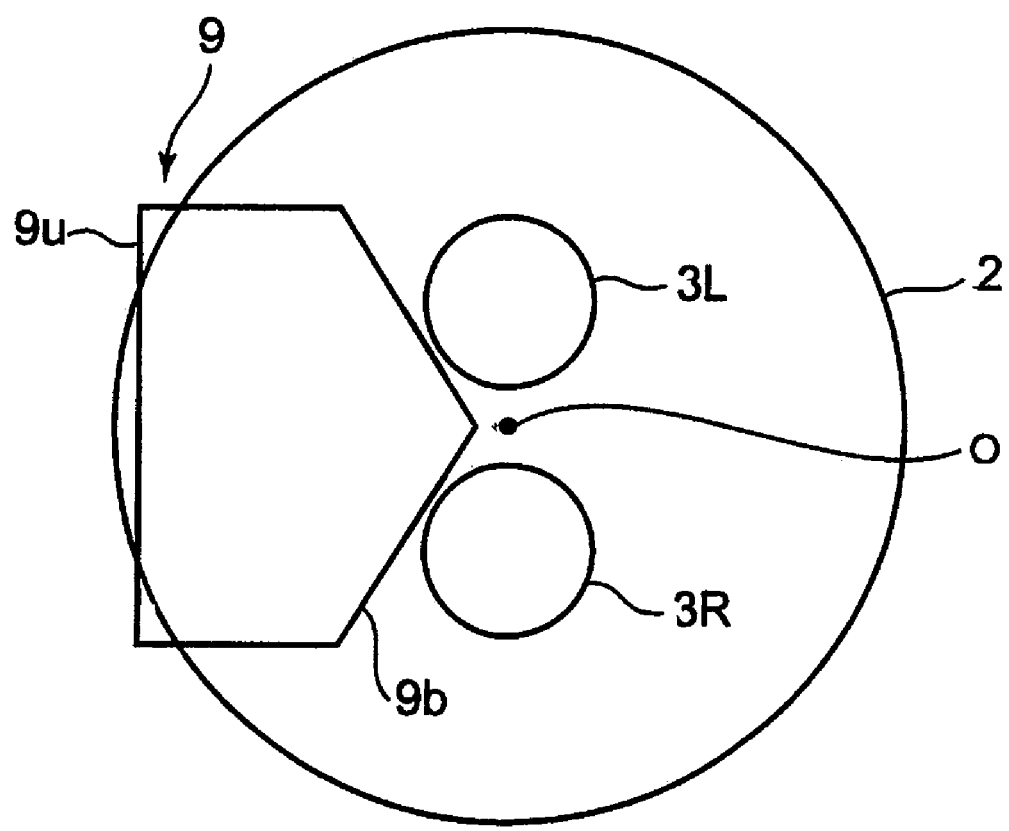
FIG. 2 is an outline diagram showing the placement of the deflection mirror of the ophthalmic microscope in Embodiment 1 of the present invention.

Next, referring to FIG. 2, the placement of the deflection mirror 9 will be explained. FIG. 2 shows the placement of each member of the objective lens 2 from a side view of the inspecting eye E. The observation optics 3 is constituted of a lens group containing those mentioned above. It is equipped with left observation optics 3L and right observation optics 3R (the pair of observation optics of the present invention). The left observation optics 3L guides the observation beam to the ocular lens of the left eye, while the right observation optics 3R guides the observation beam to the ocular lens of the right eye. Thereby the ophthalmic microscope 1 achieves binocular vision. The deflection mirror 9, as mentioned below, acts as a deflection member for guiding the illumination light to the inspecting eye E simultaneously. The deflection mirror 9 is placed between the illumination optics 8 and the observation optical axis O. The deflection mirror 9 deflects the illumination light so as to be parallel to the observation optical axis O.

In addition, the end part near the observation optical axis O of the deflection mirror 9, specifically, the lower end 9u of the deflection mirror 9 is placed in the area of the observation optical axis O. The illumination light selected by the installation position of each transparent piece of the below mentioned closure plate 6 is deflected at a different angle depending on the position of the deflection mirror 9, and then refracted by the objective lens 2 onto the observation optical axis O to become the illumination light L1, L2 and L3 respectively. Each of these illuminates the inspecting eye E having an inclination (angle to the observation optical axis O when the illumination light contacts the inspecting eye E) θ3, θ2 and θ1. The upper end 9b of the deflection mirror 9 has a triangular shape so as not to intercept the observation light beam introduced into the left observation optics 3L or the right observation optics 3R.

Figure 3A:
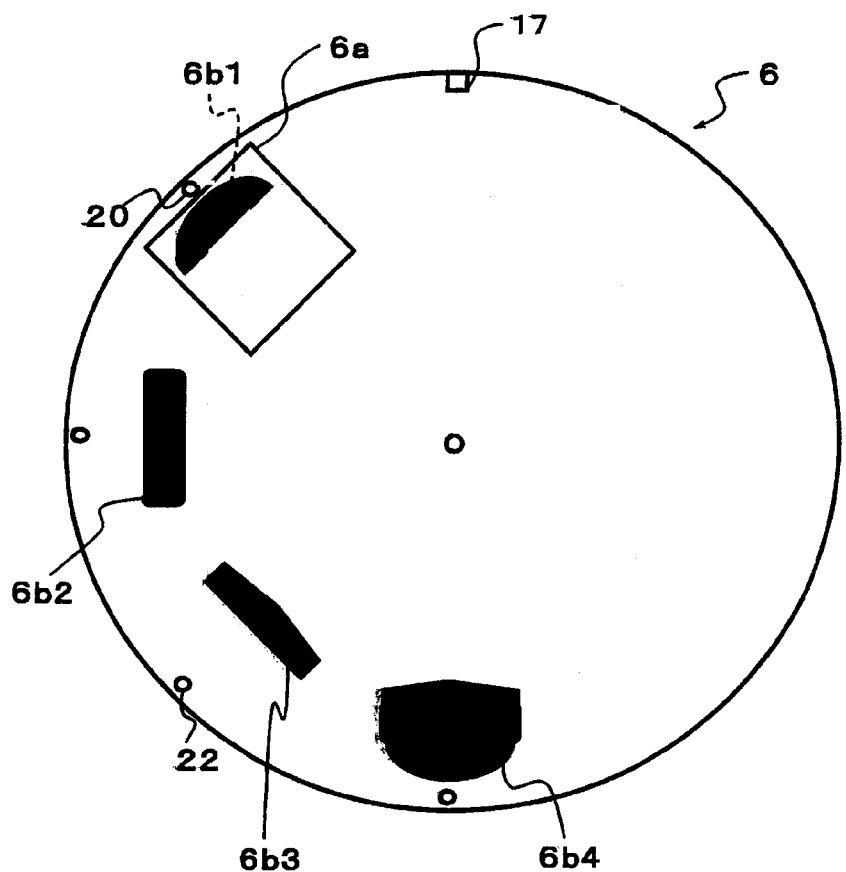
FIGS. 3A and 3B are block outline diagrams showing the closure plate and the correlated color temperature changing filter of the ophthalmic microscope in Embodiment 1 of the present invention.

Next, referring to FIGS. 3A and 3B, the structure of the closure plate 6 where the correlated color temperature changing filter 6a is located will be explained. FIG. 3A shows the closure plate 6 used with the halogen light source. As shown in FIG. 3A, the closure plate 6 has a disk shape with several transparent pieces 6b1 to 6b4 open arranged around the periphery. The transparent pieces 6b1 to 6b4 are used for switching the inclination and each have different shapes and opening positions. Rotating the closure plate 6 switches the transparent pieces 6b1 to 6b4 to select a portion of the illumination light beam from the light source 4, and the selected light is deflected by the deflection mirror 9 to become the above explained illumination light L1, L2 and L3, and thereby switching the inclination θ3, θ2 and θ1 (see FIG. 1). In addition to the transparent piece 6b1, there is also correlated color temperature changing filter 6a with a size large enough to cover the transparent piece 6b1.

The correlated color temperature changing filter 6a used here enables the correlated color temperature (3000K) of the illumination light from the halogen light source to be changed to 6000K. In addition, each position detection hole (for example, the position detection hole 20) is positioned on the line connecting the center of the closure plate 6 to the center of the transparent pieces 6b1 to 6b4 and open around the periphery nearest the closure plate 6. When controlling the operation of the closure plate 6, these position detection holes are used to detect the position of the transparent pieces 6b1 to 6b4 for switching the inclination of the illumination light with the below mentioned closure plate 6.

Figure 3B:
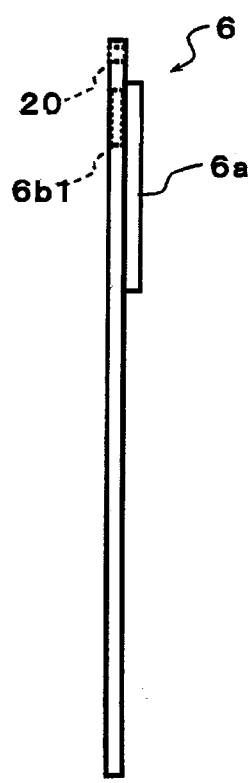

From a side view of the closure plate 6 comprising the correlated color temperature changing filter 6a the correlated color temperature changing filter 6a is located as shown in FIG. 3B. Although the details will be described below, by rotating with the driving mechanism 7, the closure plate 6 is constituted to selectively position the transparent pieces 6b1 to 6b4 for switching to the desired inclination such that they face the beam end 5a of the light guide 5. The reason why the correlated color temperature changing filter 6a is located only in the transparent piece 6b1 will be explained in detail together with the usage of this microscope in the section describing the effects of this ophthalmic microscope; however, the reason relates to cases when it is necessary to change the correlated color temperature of the illumination light of the light source 4 to illuminate at an inclination corresponding to the transparent piece 61b (for example, when conducting an examination of hypermature cataracts).

The transparent pieces 6b1 to 6b4 formed on the closure plate 6 are prepared in four patterns, including, firstly, a semi-circular transparent piece 6b1, secondly, a rectangular transparent piece 6b2, thirdly, a hexagonal transparent piece 6b3, and lastly, a transparent piece 6b4 formed by combining the shapes of 6b1 to 6b3. Of course, the position and shape of the transparent pieces on the closure plate 6 are not limited to these four types. It is possible to design the transparent piece in a shape corresponding to its purpose, such as the degree of inclination is required to radiate onto the inspecting eye E. In addition, the openings in the transparent pieces 6b1 and 6b3 are each formed such that the distance from the opening to the circular closure plate 6 is different. The illumination light is directed onto the inspecting eye E at different angles by selecting the transparent pieces 6b1 to 6b3 at different positions corresponding to said inclinations θ3, θ2 and θ1, respectively. Since the transparent piece transmits the illumination light selectively, one portion of the illumination light passes through and the other portion of the partially illumination light is intercepted. The position at which the illumination light passed through the transparent piece into the deflection mirror 9 varies for each transparent piece. Therefore, as shown in FIG. 1, the illumination light passing through the transparent piece 6b strikes the deflection mirror 9 at a different position for each transparent piece, is reflected by the deflection mirror 9, and then is directed to the inspecting eye E at a different inclination. The transparent piece 6b4 is used when observing the inspecting eye E without inclination.

Figure 4:
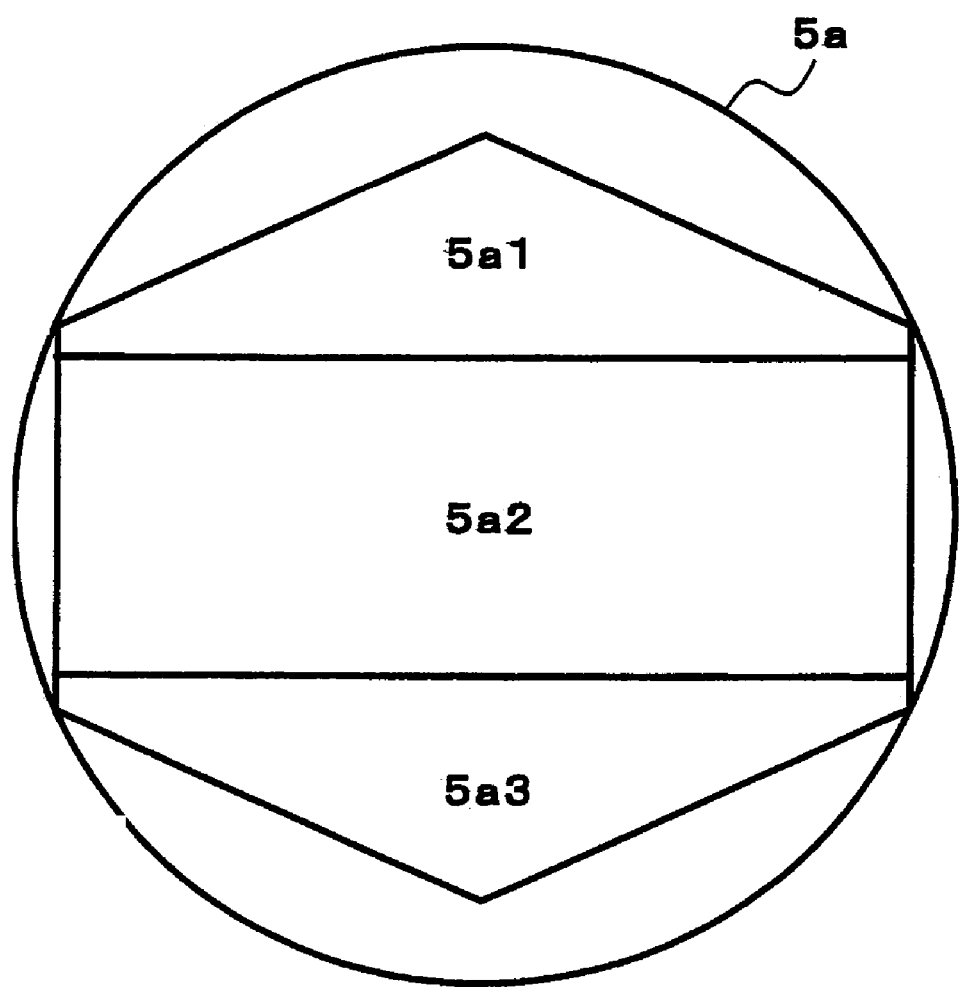
FIG. 4 is an outline diagram showing the shading of the illumination light by the closure plate of the ophthalmic microscope in Embodiment 1 of the present invention.

FIG. 4 shows, for illustrative purposes, each portion of each illumination light passing through each transparent piece of the closure plate 6, when looking at the beam end 5a of the light guide 5 over each transparent piece of the closure plate 6 from a side of the illumination optics 8. The position, shape, and size of each transparent piece is designed such that the illumination light passing through the respective transparent piece is directed to the deflection mirror 9 via the illuminated optics 8. Briefly, the closure plate 6 intercepts a portion of the illumination light from the beam end 5a that is not directed to the deflection mirror 9. When a portion of the beam of the light guide 5 is intercepted, for example, the illumination light having the area section 5a1 corresponding to the transparent piece 6b1 shown in FIG. 3A, the illumination light having the area section 5a3 corresponding to the transparent piece 6b2, the illumination light having the area 5a2 corresponding to the transparent piece 6b3, or the illumination light having the areas 5a1 to 5a3 corresponding to the transparent piece 6b4 is directed to the deflection mirror 9.

Meanwhile, the illumination optics 8 are constituted as odd times of imaging optics. Since the image of the illumination light beam is provided at odd times, the image turns out upside down (an upside down image). For example, when using the closure plate 6 shown in FIG. 3A, the illumination light passing through the transparent piece 6b1 is reflected onto the deflection mirror 9 as shown in FIG. 1 and becomes the illumination light L3 via the objective lens 2 to illuminate the inspecting eye E having approximately 6° of inclination θ3. In addition, the illumination light passing through the transparent pieces 6b2 and 6b3 becomes the illumination light L2 and L1, respectively, to illuminate the inspecting eye E having approximately 4° and 2° of inclination θ2, θ1, respectively.

Figure 5:
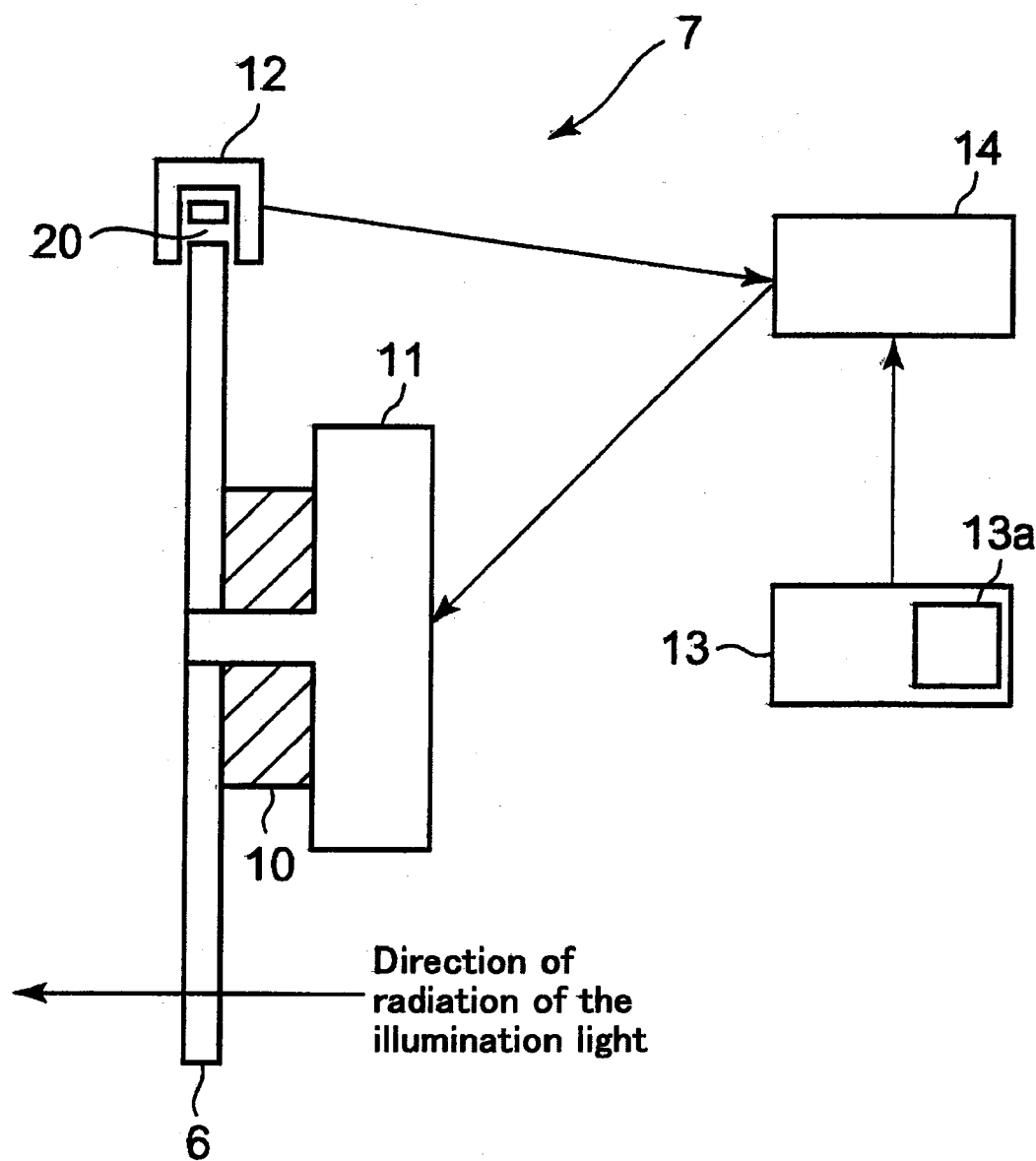
FIG. 5 is a block outline diagram showing the driving mechanism of the ophthalmic microscope in Embodiment 1 of the present invention.

FIG. 5 shows the outlined structure of the driving mechanism 7. The driving mechanism 7 constitutes a beam area adjustment means for adjusting the closure plate 6 where the correlated color temperature changing filter 6a is located (the correlated color temperature changing filter 6a is not shown), as well as the area of the illumination light beam, for selecting any of the transparent pieces 6b1 to 6b4 by rotating the closure plate 6.

The driving mechanism 7 selectively adjusts each transparent piece of the closure plate 6 to face the beam end 5a of the light guide 5 by manipulating the mounting member 10 and rotating the closure plate 6 utilizing the rotation drive of the stepping motor 11 mounted on the closure plate 6 on which the position detection hole 20 is formed. The photo sensor 12, the foot pedal 13, and the control circuit 14 are provided to control the drive of the stepping motor 11. The photo sensor 12 is a position detection means for detecting the rotation position of each position detection hole on the closure plate 6 (for example, the transparent piece 20) and is located so as to sandwich the periphery of the closure plate 6 (including each position detection hole). The foot pedal 13 is a pedal operable means for controlling the performance of the stepping motor 11. The foot pedal 13 includes a switch button 13a for determining the switching of the inclination of the illumination light and to change the correlated color temperature simultaneously. In addition, the control circuit 14 controls the rotation angle of the stepping motor 11 according to the control signal based on the determination of the inclination of the illumination light by the pedal operation of the foot pedal 13 and the detection signal based on the current position of each position detection hole detected by the photo sensor 12.

In FIG. 5, the closure plate 6 is rotated by the stepping motor 11. However, if the rotation axis of the stepping motor 11 and that of the closure plate 6 are positioned eccentrically, a gear structure, a power transmission structure including a timing belt, and a power transmission member are manipulated along the rotation axis to transmit the rotation power from the stepping motor 11 to the closure plate 6, thereby increasing the degree of freedom in the placement of the stepping motor 11. Furthermore, since it becomes possible to shorten the distance from the rotation axis to each transparent piece on the closure plate 6 regardless of the outer diameter of the stepping motor 11, it is possible to decrease the distance of each transparent piece to the rotation angle of the closure plate 6, thereby easing the required accuracy of the position of each transparent piece.

It is also possible to switch each transparent piece manually by mounting a manual knob (not shown) on the closure plate 6. In addition, the method of controlling the rotation angle of the closure plate 6 for determining the inclination includes memorization of the degree of the (rotation) angle formed by the original point (optional) and the central point of each transparent piece and using the control circuit 14 to control the operation of the stepping motor 11 based on the degree of the angle such that the desired transparent piece faces the beam end 5a of the light guide 5.

(Operation/Effect of the Ophthalmic Microscope)

According to the ophthalmic microscope including the structure discussed above, it becomes possible to perform an observation of the inspecting eye as follows.

Herein, an inspecting eye E suffering from cataracts will be explained for the purpose of example. Regarding cataracts, as mentioned above, since the observation conditions vary depending on the progression of the cataracts, a case of common cataracts will be exemplified. When observing the inspecting eye E suffering from common cataracts, the observation is performed using a red reflex from said complete coaxis lighting (2°inclination). In this case, it is necessary to observe under a correlated color temperature of 3000K of the illumination light. When using the ophthalmic microscope, the illumination light from the halogen light source can be utilized as is. Accordingly, the transparent piece 6b3 with the illumination light at 2° inclination (corresponding to θ1 in FIG. 1) is adjusted to face the beam end 5a of the light guide 5 without using the correlated color temperature changing filter 6a on the closure plate 6 shown in FIG. 3A.

First, the switch button 13a contained in the foot pedal 13 shown in FIG. 5 is pedal operated to send the control signal to the control circuit 14. In order to observe the inspecting eye E under the complete coaxis lighting as mentioned above, the inclination must be set to 2°. The examiner or the operator adjusts the inclination to 2° by performing a single pedal operation on the switch button 13a. The pedal operation allows receipt of the detection signal based on the position detection hole 22 from the photo sensor 12, and the control circuit 14 determines the current position of the closure plate 6 facing the beam end 5a (rotation angle) to control the rotation angle of the stepping motor 11 such that the transparent piece 6b3 corresponding to the 2° inclination is moved from its current position to be positioned in the position detection hole through which the light passes. This causes the transparent piece 6b3 on the closure plate 6 to face the beam end 5a of the light guide 5. The illumination light passing through the transparent piece 6b3 is directed by the illumination optics 8 to hit the deflection mirror 9. Thereafter, the illumination light reflected onto the deflection mirror 9 and deflected in the parallel direction to the observation optical axis O is refracted by the objective lens 2, and thereby, the deflection mirror 9 illuminates the inspecting eye E with illumination light having 2° of inclination θ1 to the observation optical axis O.

Figure 6:
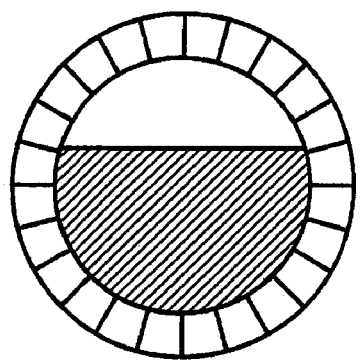
FIG. 6 is a diagram showing the quality of red reflex obtained by the ophthalmic microscope in Embodiment 1 of the present invention.

FIG. 6 shows the outline of the red reflex obtained by the illumination light directed by the deflection mirror 9. The red reflex indicated as the shaded area in the same figure shows the state seen by the examiner looking through the ocular lens to view the inspecting eye E. Herein, the examiner and the operator perform the observation while standing on the opposite side of the light source 4 on the observation optical axis O. The radially lined part in the periphery of the same figure indicates the iris of the inspecting eye E.

Since this illumination light contacts the inspecting eye E at an inclination of 2° (+2°) on the side opposite where the examiner or the operator is standing, the light mainly illuminates the examiner's side (negative direction) of the retina of the inspecting eye E, generating an area where the red reflex cannot be obtained on the side of the light source 4. If it is desired to further decrease the area without the red reflex, it is possible to increase the number of deflection mirrors to be provided. Since Patent laid-open No. 2004-139002 contains such an explanation, detailed descriptions will be omitted herein.

Next, we will describe a case of observing an inspecting eye E suffering from hypermature cataracts using the ophthalmic microscope. When performing CCC as mentioned above, the reflected light cannot be observed since the entire lens is clouded. Therefore, it is necessary to observe the reflected light from the capsule of the lens using angle lighting, without using the red reflex from the complete coaxis lighting. In this case, the inclination is approximately 6° depending on the degree of cloudiness of the inspecting eye E (hereinafter, described as 6° inclination). However, since the capsule of the lens has extremely high transparency and low reflection intensity, it must be observed using a short wavelength light (correlated color temperature of approximately 6000K). Therefore, using the correlated color temperature changing filter 6a shown in FIG. 3A on the closure plate 6 to change the correlated color temperature of the illumination light (3000K) to 6000K causes the transparent piece 6b1 corresponding to the 6° inclination (corresponding to θ3 in FIG. 1) to face the beam end 5a of the light guide 5. Observation procedures for examination of cases than the inspecting eye E suffering from common cataracts will be explained below.

First, a pedal operation is performed on the switch button 13a contained in the foot pedal 13 shown in FIG. 5, and the rotation angle of the stepping motor 11 is controlled such that the transparent piece 6b1 with the 6° inclination is positioned in the position detection hole 20 through which the light passes. This causes the correlated color temperature changing filter 6a on the transparent piece 6b1 of the closure plate 6 to face the beam end 5a of the light guide 5. The illumination light passing through the transparent piece 6b1 and the correlated color temperature changing filter 6a is directed by the illumination optics 8 and reflected onto the deflection mirror 9. Thereafter, the illumination light reflected onto the deflection mirror 9 and deflected in the parallel direction on the observation optical axis O is refracted by the objective lens 2, thereby, the deflection mirror 9 illuminates the inspecting eye E with the illumination light having 6° of inclination θ3 to the observation optical axis O.

As mentioned above, the ophthalmic microscope of the present embodiment enables the observation of the inspecting eye by designating the use or non-use of the correlated color temperature changing filter on the closure plate depending on the circumstances using a simple operation. In addition, control of the correlated color temperature changing filter becomes possible through rotation of the closure plate operating in conjunction with the correlated color temperature changing filter in a simple structure, wherein the closure plate that can be switched to the desired inclination is constituted together with the correlated color temperature changing filter. Therefore, the structure allows the switching and changing of the inclination and the correlated color temperature using a simple operation.

Embodiment 2

In Embodiment 1, an ophthalmic microscope equipped with a halogen light source was explained for the purpose of example. It is also possible to place a xenon light source in the ophthalmic microscope of said Embodiment 1 and Embodiments 3 and 4 mentioned below. Furthermore, since the components are almost the same except for the xenon light source and the closure plate 61 shown in FIG. 7, only different components will be explained to clarify the difference from Embodiment 1.

Figure 7:
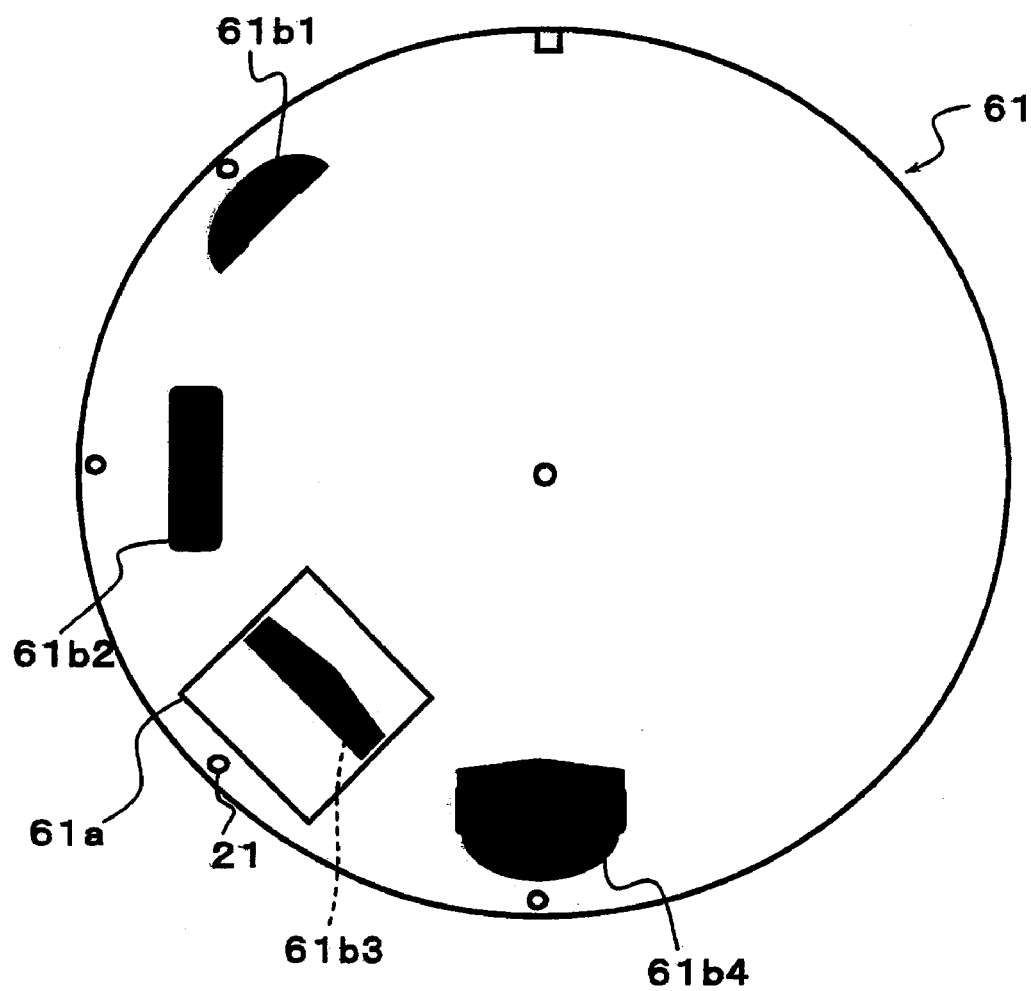
FIG. 7 is a block outline diagram showing the closure plate and the correlated color temperature changing filter of the ophthalmic microscope in Embodiment 2 of the present invention and a front view of the closure plate and said correlated color temperature changing filter using a xenon light source.

When using the ophthalmic microscope equipped with a xenon light source, the correlated color temperature changing filter is used to change the correlated color temperature of the illumination light from 6000K to 3000K. The closure plate 61 formed in a disc shape, as shown in FIG. 7 for example, is used as the correlated color temperature changing means. Similar to the closure plate 6 (see FIG. 3A), the transparent pieces 61b1 to 61b4 are open near the periphery of the closure plate 61. The transparent pieces 61b1 to 61b4 act to switch the inclination and each have different shapes and different positions of the openings. The correlated color temperature changing filter 61a is provided that is large enough to cover the transparent piece 61b3. The correlated color temperature changing filter 61 used here can change the correlated color temperature of the illumination light from the xenon light source (6000K) to 3000K.

The reason why the correlated color temperature changing filter 6a is located only in the transparent piece 6b1 relates to cases when it is necessary to change the correlated color temperature of the illumination light of the light source 4 and illuminate at an inclination corresponding to the transparent piece 6b3 (for example, observation of hypermature cataracts).

In addition, each position detection hole (for example, the position detection hole 21) is positioned on the line connecting the center of the closure plate 61 to the center of the transparent pieces 61b1 to 61b4, and open around the periphery nearest to the closure plate 61. The position detection holes are used to detect the position of the transparent pieces 61b1 to 61b4 when controlling the closure plate 61 for switching the inclination of the below mentioned illumination light. Similar to the closure plate 6 used in the ophthalmic microscope equipped with the halogen light source, the transparent pieces 61b1 to 61b4 formed on the closure plate 61 have 4 patterns. The shape and function of each transparent piece is the same as that of closure plate 6, for example, 6b1 corresponds to 61b1. In addition, the driving mechanism 7 can be used for the closure plate 61 in a similar way as in the embodiment using the xenon light source (see FIG. 7). In the description of the observation method using this ophthalmic microscope, the closure plate 61 of Embodiment 1 is simply referred to as the closure plate 61, thus we will omit the explanation herein.

Embodiment 3

(Structure of Each Part and the Entire Ophthalmic Microscope)

Embodiment 3 of the present invention is an ophthalmic microscope comprising a closure plate containing a correlated color temperature changing filter which is a component of the correlated color temperature changing means, and a transparent piece which is a component of the lighting angle switching means, different from the constitution of the microscope of Embodiment 1, wherein the color temperature changing means and the lighting angle switching means are separately constituted.

Figure 8:
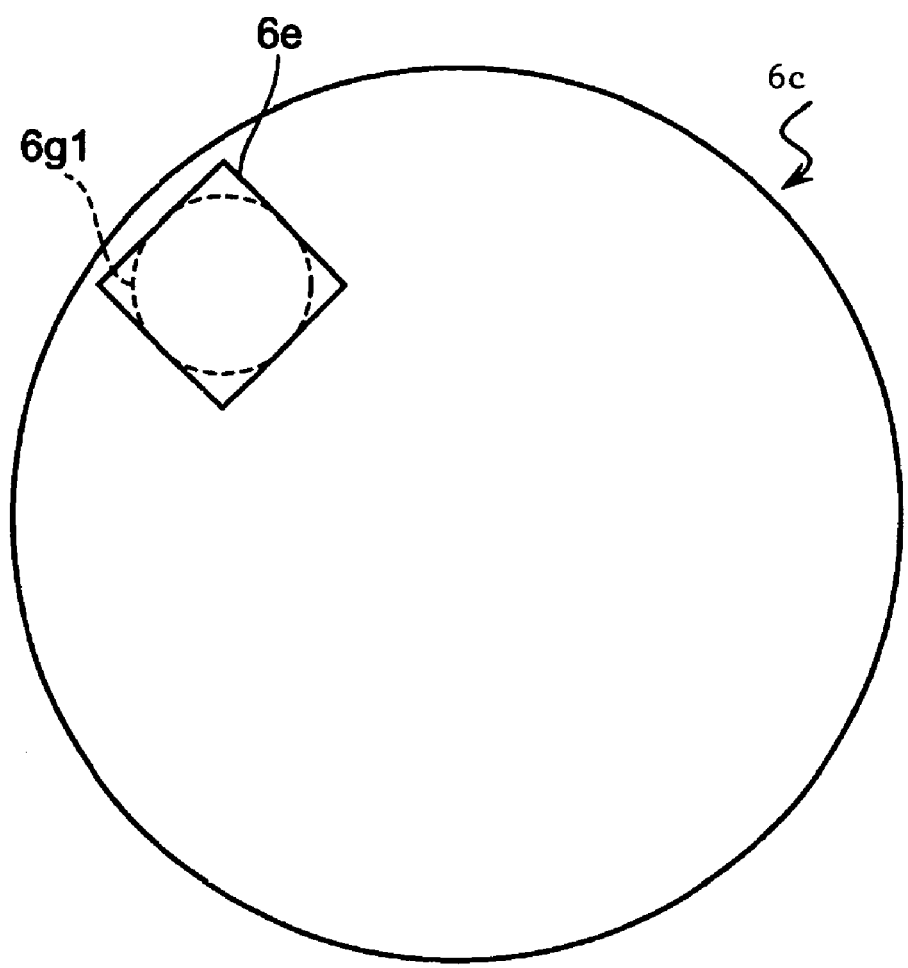
FIG. 8 is a block outline diagram showing the correlated color temperature changing filter of the ophthalmic microscope in Embodiment 3 of the present invention and a front view of the correlated color temperature changing filter placed on the substrate.
Figure 9:
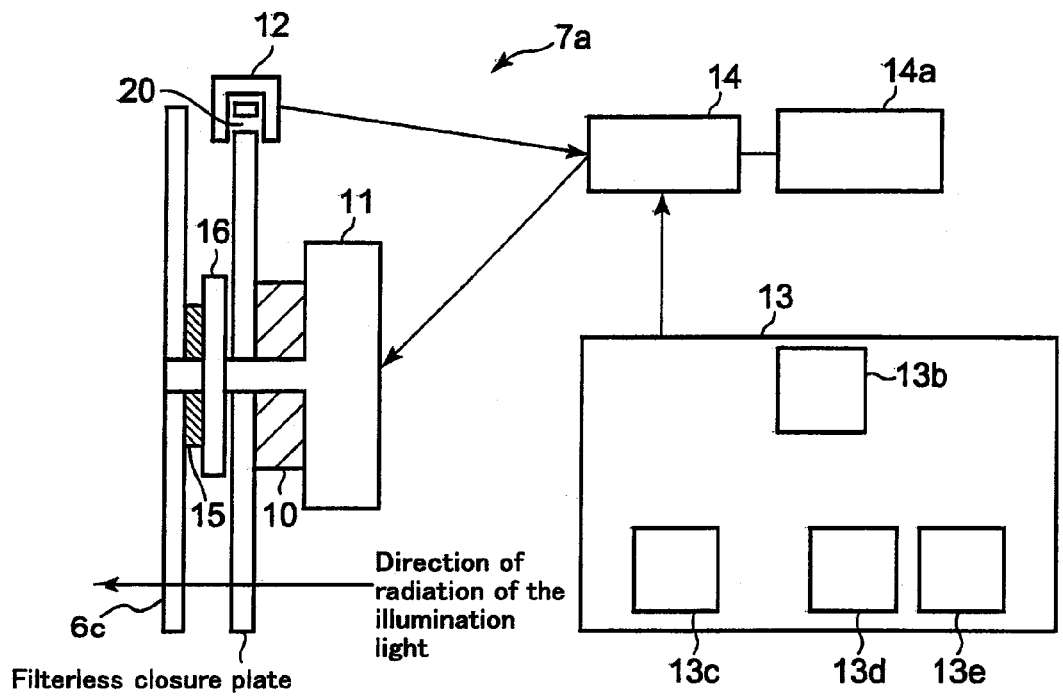
FIG. 9 is a block outline diagram showing a driving mechanism containing the correlated color temperature changing filter of the ophthalmic microscope in Embodiment 3 of the present invention.

The difference from the ophthalmic microscope of Embodiment 1 is that the ophthalmic microscope comprises the closure plate 6 and said correlated color temperature changing filter 6a shown in FIG. 3A as individual components, wherein the closure plate 6 works in conjunction with the correlated color temperature changing filter 6a to drive. The closure plate 6 used in the explanation, i.e., the closure plate 6 on which the correlated color temperature changing filter 6a is placed shown in FIG. 3A, is removed. Referring to FIG. 8 and FIG. 9, the components different from those of Embodiment 1 will be explained below.

First, regarding the entire structure of the ophthalmic microscope of Embodiment 3, we will explain the different components with reference to FIG. 1. Those components not explained here are the same as those shown in FIG. 1. The closure plate containing a transparent piece, which is a component of the lighting angle switching means, has a structure not including the correlated color temperature changing filter 6a of the closure plate 6 shown in FIG. 3A and is equivalent to the closure plate 6 shown in FIG. 1. Hereinafter, the closure plate 6 is referred to as "the filterless closure plate 6" (see FIG. 8).

In addition, the correlated color temperature changing filter, which is a component of the color temperature changing means as shown in FIG. 8, includes the correlated color temperature changing filter 6e that is large enough to cover the opening 6g1 of the substrate 6c and is equivalent to the correlated color temperature changing filter 6a shown in FIG. 1. Furthermore, there is a driving mechanism 7a comprising a driving means for driving the closure plate and the correlated color temperature changing filter, as well as a control means for instructing the concurrent driving of the driving means, which is equivalent to the driving mechanism 7 shown in FIG. 1.

Next, each component different from those in Embodiment 1 will be explained. Together with the explanation of the structure of the substrate 6c on which each correlated color temperature changing filter of FIG. 8 is placed, we have shown the driving mechanism 7a, indicated by the outlined structure in FIG. 9, containing the correlated color temperature changing filter of the embodiment of the present invention, and will now explain the structure of the driving mechanism 7a for driving the rotation of said closure plate 6 and said substrate 6.

First, we will explain the detailed structure the substrate 6c shown in FIG. 8, i.e., the correlated color temperature changing filter that is a component of the color temperature changing means placed on the ophthalmic microscope of Embodiment 2. As mentioned above, the correlated color temperature changing filter that is a component of the ophthalmic microscope of Embodiment 1 is constituted together with the closure plate 6 shown in FIG. 3A. However, the correlated color temperature changing filter located in the ophthalmic microscope of Embodiment 3 is constituted separately from the closure plate and placed on the substrate 6c as shown in FIG. 9.

The substrate 6c is a transparent and colorless substrate constituted in a circular shape. Therefore, the illumination light can be transmitted regardless of the kinds of light bulb of the light source. As shown in FIG. 8, the substrate 6c has an opening 6g1 consisting of a cutout hole symmetrical to the center as an axis. The opening 6g1 has a correlated color temperature changing filter 6e that is large enough to cover the opening. The correlated color temperature changing filter 6e located in the opening 6g1 is designed to be large enough to cover the transparent piece 6b1 of said filterless closure plate 6 (with 6° inclination). Consequently, for example, the illumination light passing through the transparent piece 6b1 located on the filterless closure plate 6 passes through the correlated color temperature changing filter 6e located on the opening 6g1. Thus, the correlated color temperature of the illumination light can be changed by the correlated color temperature changing filter 6e by switching the inclination (6° in this case). In addition, since the components other than the opening 6g1 and the correlated color temperature changing filter 6e are transparent and colorless, when the correlated color temperature is not changed (when the correlated color temperature changing filters are not used), the substrate 6c is rotated by the below mentioned driving means and the illumination light passing through the transparent and colorless parts of the substrate 6c (hereinafter, referred to as "the transparent pieces") is used to perform the observation of the inspecting eye.

Furthermore, the correlated color temperature changing filter 6e enables the correlated color temperature of the illumination light to be changed from the 3000K halogen light source to 6000K. The correlated color temperature changing filter 6e enables the correlated color temperature of the illumination light to be changed from the 3000K halogen light source to 6000K. By providing a correlated color temperature changing filter with such characteristics, one microscope can be used in cases when, for example, it is necessary to change the correlated color temperature of the illumination light depending on the progression of the medical condition, such as cataracts.

Next, we will explain the detailed structure of the drive control means of the closure plate in the ophthalmic microscope of Embodiment 3, including the correlated color temperature changing filter, which is a component of the correlated color temperature changing means, as well as the transparent piece, which is a component of the lighting angle switching means, both of which compose the driving mechanism 7a shown in FIG. 9. The driving mechanism 7a shown in FIG. 9 selectively arranges each correlated color temperature changing filter of the substrate 6c and each transparent piece of the filterless closure plate 6 so as to face the beam end 5a of the light guide 5 by rotating the substrate 6c and the filterless closure plate 6 using the rotation drive of the stepping motor 11, which is the driving means for operating both the clutch 16 mounted on the substrate 6c and manipulated by the mounting member 15 and the filterless closure plate 6 placed on the position detection hole and manipulated by the mounting member 10.

As shown in FIG. 9, the filterless closure plate 6 and the substrate 6c are located back and forth to the direction of the illumination light radiation from the light source. Briefly, the illumination light first passes through the filterless closure plate 6, then through the substrate 6c (FIG. 8 shows the opposite direction of FIG. 1). Referring to FIG. 1, the substrate 6c is placed on the optical axis of the illumination light L on the deflection mirror side. In addition, the filterless closure plate 6 is placed on the light guide 5 side. The filterless closure plate 6 contains the stepping motor 11 mounted on the filterless closure plate 6 and manipulated by the mounting member 10 and the clutch 16 mounted on the axis of the substrate 6c on which the correlated color temperature changing filter 6e is placed and manipulated by the mounting member 15. The photo sensor 12, the foot pedal 13, and the control circuit 14 are installed to control the rotation of said stepping motor 11. Furthermore, the operation means for operating the control circuit 14 includes the foot pedal 13 which is constituted to contain the filterless button 13b, the 2° inclination button 13c, the 4° inclination button 13d and the 6° inclination button 13e, each being switched to send a signal to the control circuit 14 to control each inclination.

The stepping motor 11 is a driving means for operating the filterless closure plate 6. The filterless closure plate 6 rotates according to the rotation of the stepping motor 11. When the clutch 16 is engaged to connect the filterless closure plate 6 and the substrate 6c, the filterless closure plate 6 and the substrate 6c rotate in conjunction with the rotation of the stepping motor 11. If the clutch 16 is disengaged to disconnect the filterless closure plate 6 from the substrate 6c, as mentioned above, the filterless closure plate 6 will rotate separately. This allows for the filterless closure plate 6 to either operate in conjunction with the substrate 6c or operate separately. Accordingly, the same operation applies to the transparent piece of the substrate 6c. The mechanism between the rotation axis of the stepping motor 11 and the filterless closure plate 6 and the substrate 6c enables the observation of the inspecting eye E using either the gear structure or the like or the manual knob. 6c or operate separately. Accordingly, the same operation applies to the transparent piece of the substrate 6c. The mechanism between the rotation axis of the stepping motor 11 and the filterless closure plate 6 and the substrate 6c enables the observation of the inspecting eye E using either the gear structure or the like or the manual knob.

Meanwhile, rather than the below-mentioned clutch 16, the control circuit 14 including, for example, the driving means for separately rotating the substrate 6c including the stepping motor, and a sensor for controlling the rotation of the substrate 6c (not shown) may be used to control the adjustment using a combination of control conditions (interface table 14a) shown in FIG. 9 memorized by the control circuit 14 (a combination of condition for changing the correlated color temperature changing filter and the switching angle).

The filterless closure plate 6, the substrate 6c and the driving mechanism 7a have a structure similar to the closure plate 6 component of the ophthalmic microscope in Embodiment 1. Thus it is possible to change the correlated color temperature and switch the inclination simultaneously. For example, when observing common cataracts, the transparent piece 6b3 located on the filterless closure plate 6 (at 2° herein) and the transparent piece of the substrate 6c both face the beam end 5a of the light guide 5. When observing the hypermature cataracts, it is possible to observe the inspecting eye E by selectively aligning the transparent piece 6b1 on the filterless closure plate 6 (equivalent to 6° herein) and the correlated color temperature changing filter 6e on the filterless closure plate 6 so as to face the beam end 5a of the light guide (see FIG. 4). In addition, due to the structure of the ophthalmic microscope of Embodiment 3, one microscope can be employed for cases when, for example, it is necessary to switch the inclination and change the correlated color temperature of the illumination light depending on the progression of the medical condition, such as cataracts.

(Operation/effect of the Ophthalmic Microscope)

The ophthalmic microscope of the present embodiment having the aforementioned structure enables the observation of the inspecting eye as follows.

For example, in the observation of cataracts, the observation of the inspecting eye E with common cataracts uses a red reflex from the complete coaxis lighting (at 2° inclination) and, as mentioned above, a correlated color temperature of 3000K of the illumination light. In addition, when observing the inspecting eye E with hypermature cataracts, the observation is performed using the angle lighting (at 6° inclination) and, as mentioned above, a correlated color temperature of 6000K of the illumination light.

First, we will explain the observation procedures for observing an inspecting eye E with common cataracts. The following makes reference to FIG. 9 (drive control procedures for the filterless closure plate 6 and the substrate 6c). Observation of the inspecting eye E with common cataracts, as mentioned above, can be performed by switching the inclination of the illumination light to 2° with a correlated color temperature of 3000K as mentioned above. Therefore, the observation is performed without changing the correlated color temperature. Considering the cutout 17 on the filterless closure plate 6 (see FIG. 3A) to be the base position, the control circuit 14 sends a control signal (electric signal) to rotate the stepping motor 11 based on the position of said cutout 17. For example, the control circuit 14 adjusts the rotation such that the inclination is 2° and the corresponding transparent piece 6b3 faces the optical axis of the illumination light. This causes the transparent piece 6b3 to face the beam end 5a of the light guide 5 (see FIG. 4) (S2, S3).

Figure 10:
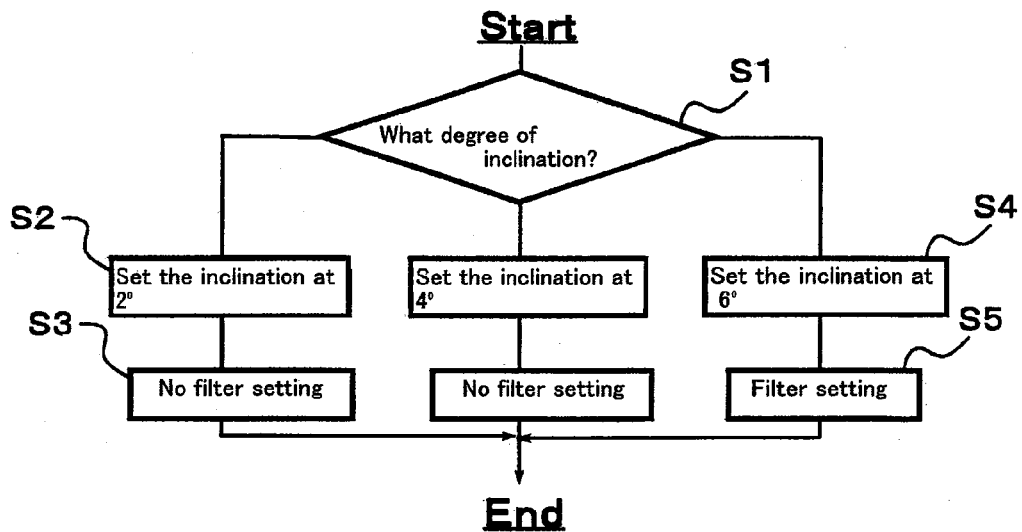
FIG. 10 is a flow chart diagram showing the drive control operation of the closure plate and the correlated color temperature changing filter in Embodiment 3 of the present invention.

Other than the above-described method, it is also possible to switch to a desired inclination by switching the position of each transparent piece without involving the cutout 17. In this case, as shown in FIG. 10, after pressing the 2° inclination button 13c shown in FIG. 9 to change the inclination, an electric signal is sent to the control circuit 14 to adjust the inclination to 2° (S1). From the electric signal obtained by the photo sensor 12 based on the light passing through each position detection hole, the control circuit determines whether the filterless closure plate 6 (rotation angle) is at the desired angle (herein, the position detection hole 22 indicates the transparent piece 6b3 having 2° inclination). If not, the control circuit controls the rotation of the stepping motor 11 such that said filterless closure plate 6 is positioned at the desired angle when the light passes through the position detection hole 22.

Furthermore, the substrate 6c is normally placed such that the correlated color temperature changing filter 6e overlaps with the substrate 6c so as to match the position of the transparent piece 6b1 of the filterless closure plate 6, the substrate 6c being connected by engaging the clutch 16. Therefore, the transparent piece of the substrate 6c is always located so as to overlap with said transparent piece 6b3. Consequently, this ophthalmic microscope is able to determine the presence or absence of the correlated color temperature changing filter while setting the desired inclination (S2) and to designate the correlated color temperature changing filter in accordance with the inclination (S3). Thereby, the illumination light passing through the transparent piece 6b3 and the transparent piece (2° inclination, 3000K correlated color temperature) is directed by the illumination optics 8 to be reflected onto the deflection mirror 9. Then, the illumination light is reflected by the deflection mirror 9 and deflected in the parallel direction to the observation optical axis O to be refracted by the objective lens 2, thereby the deflection mirror 9 illuminates the inspecting eye E with (2°) inclination θ1 on the observation optical axis O such that the operator or examiner can observe the inspecting eye E.

Different from the observation of common cataracts, the observation of an inspecting eye E suffering from the hypermature cataracts uses the transparent piece 6b1 on the filterless closure plate 6. This is because, as mentioned above, when observing hypermature cataracts, it is necessary to switch the inclination of the illumination light to 6° and change the correlated color temperature to 6000K in order to perform the observation. As mentioned above, the substrate 6c is normally located such that the correlated color temperature changing filter 6e overlaps with the substrate 6c to match the position of the transparent piece 6b1 of the filterless closure plate 6, the substrate 6c being connected by engaging the clutch 16. Therefore, it is determined that the correlated color temperature changing filter is present (S5) while the inclination is 6° (S4). Accordingly, as mentioned above, after the substrate 6c and the filterless closure plate 6 rotate, the illumination light passed through the transparent piece 6b1 and the correlated color temperature changing filter 6e (the inclination 6°, the correlated color temperature 6,000K) is directed by the illumination optics 8 to be reflected onto the deflection mirror 9. Thereafter, the illumination light reflected by the deflection mirror 9 and deflected in the parallel direction to the observation optical axis O is refracted by the objective lens 2, and thereby the deflection mirror 9 illuminates the inspecting eye E with (6°) inclination θ3 on the observation optical axis O such that the operator or examiner can observe the inspecting eye E.

Using the ophthalmic microscope of Embodiment 3, after the examiner or operator simply sets the desired inclination, the correlated color temperature is changed automatically in accordance with the inclination. That is, similar to the ophthalmic microscope of Embodiment 1, the observation of an inspecting eye E can be performed with one simple adjustment of the microscope.

Embodiment 4

(Structure of Each Part and the Entire Ophthalmic Microscope)

Figure 11:
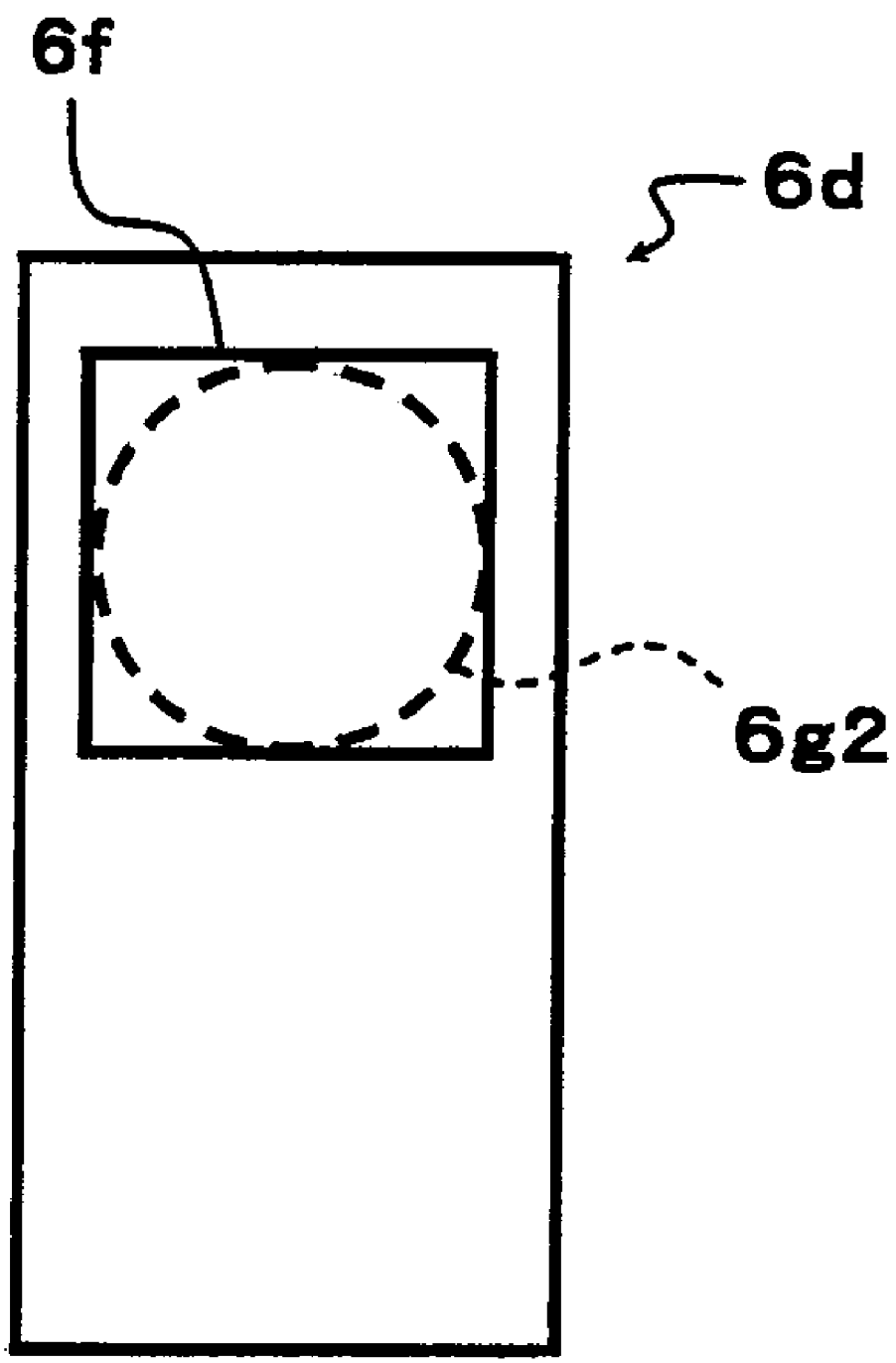
FIG. 11 is a block outline diagram showing the correlated color temperature changing filter of the ophthalmic microscope in the other embodiments of Embodiment 4 of the present invention and a front view of the correlated color temperature changing filter placed on the element.

Embodiment 4 of the present invention is an ophthalmic microscope containing a correlated color temperature changing filter which is a component of a different correlated color temperature changing means than that in Embodiment 3 shown in FIG. 11, a driving means for driving the different correlated color temperature changing filter, and a control means for directing the driving means operating in conjunction with other driving means different from those in Embodiment 3. The correlated color temperature changing filter shown in FIG. 11 is not located on the substrate 6c shown in FIG. 8 as explained in Embodiment 3, but on the element 6d. In addition, the driving means and control means will be described below in reference with the FIG. 12 and FIG. 13.

Figure 12:
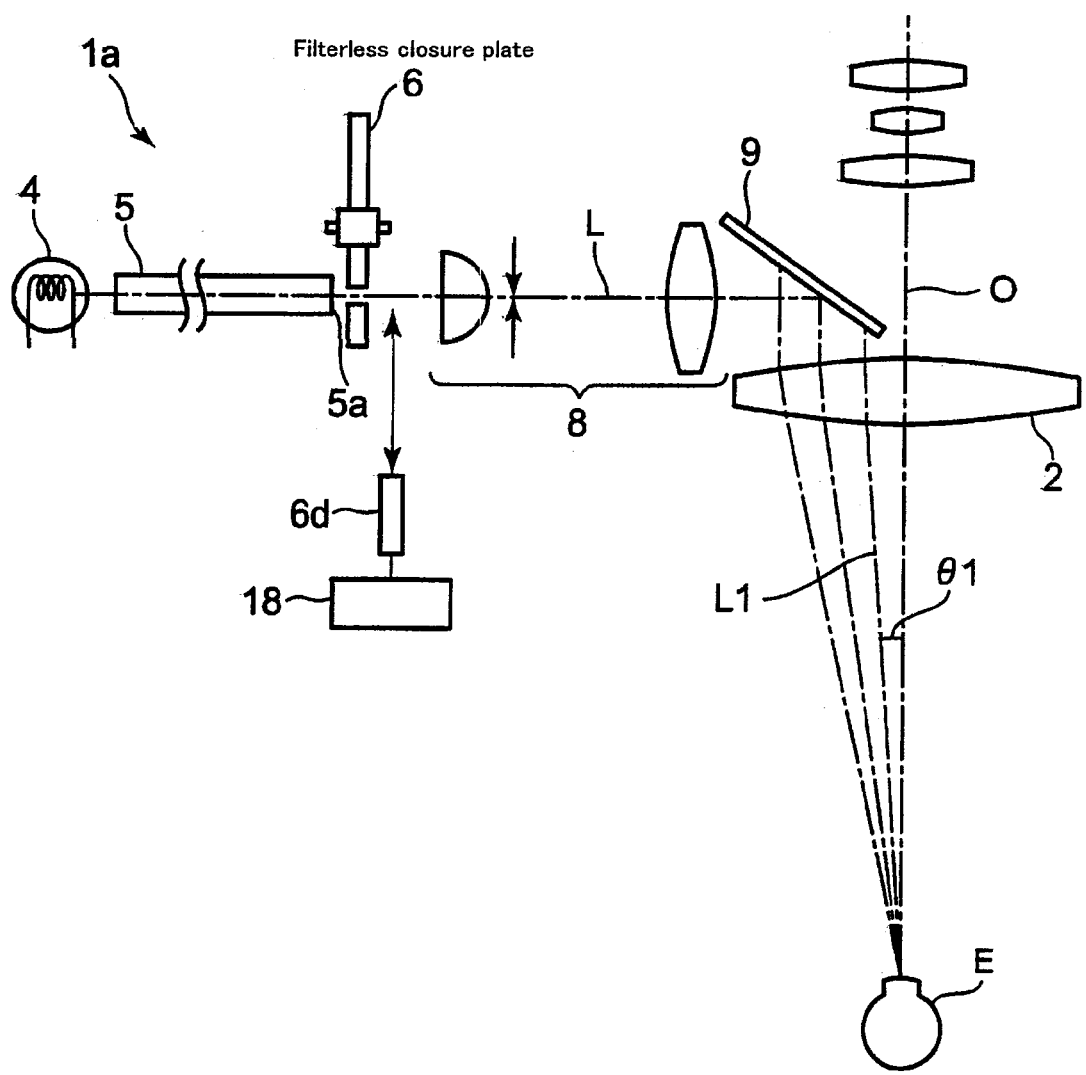
FIG. 12 is a block outline diagram showing the ophthalmic microscope in Embodiment 4 of the present invention.
Figures 13, 14:
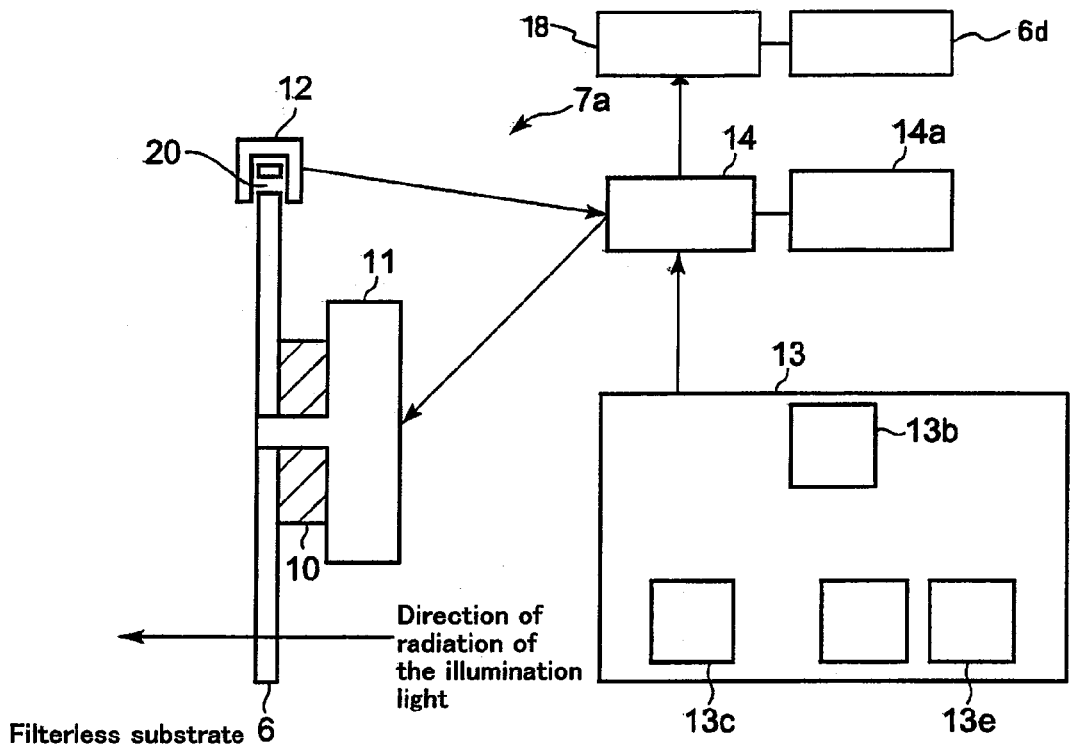
FIG. 13 is a block outline diagram showing a driving mechanism containing the correlated color temperature changing filter of the ophthalmic microscope in Embodiment 4 of the present invention.
FIG. 14 is an illustration of the interface table contained in the driving mechanism of the ophthalmic microscope in Embodiment 4 of the present invention.

Among the components of the ophthalmic microscope 1a in Embodiment 4 of the present invention shown in FIG. 12, the components different from Embodiment 3 include the transferable element 6d on which the correlated color temperature changing filter 6f shown in FIG. 11 is placed, the electromagnetic solenoid for driving said element 6d, and the control circuit 14 shown in FIG. 13 for controlling the operation of the electromagnetic solenoid 18. The element 6d or the like is contained as a component in place of the filterless closure plate 6 (where the correlated color temperature changing filter 6a placed on the closure plate 6 as shown in FIG. 3A has been removed) and the substrate 6c or the like. The other components are the same as those of the ophthalmic microscope of Embodiment 3. We will explain the structure of each component of the ophthalmic microscope in Embodiment 4 below.

The element 6d shown in FIG. 11 is equipped with an opening 6g2 corresponding to the position where the transparent pieces 6b1 to 6b4 on said filterless closure plate 6 face the beam end 5a of the light guide (see FIG. 4). The opening 6g2 and the correlated color temperature changing filter 6f located in the opening 6g2 are designed to overlap with each other and be large enough to cover the transparent pieces 6b1 to 6b4. The element 6d, as shown in FIG. 12, is placed so as to be transferable on the optical axis of the illumination light L by the operation of the electromagnetic solenoid 18. Thereby the illumination light passing though the transparent pieces 6b1 to 6b4 passes through the opening 6g2 and the correlated color temperature changing filter 6f placed in the opening 6g2, making it possible to change the correlated color temperature of the illumination light.

When the correlated color temperature changing filter 6f is not used (when not changing the correlated color temperature), the inspecting eye E is observed using only the filterless closure plate 6 rather than the element 6d. In addition, it is necessary to design the correlated color temperature changing filter 6f appropriately depending on the circumstances, for example, such that the correlated color temperature of the illumination light is 3000K when observing common cataracts and 6000K when observing hypermature cataracts. Furthermore, the electromagnetic solenoid 18 is used to operate the element 6d. The electromagnetic solenoid 18 comprises the control circuit 14 and the foot pedal 13 for operating the element 6d as shown in FIG. 13. Since the structure of the control circuit 14 shown in FIG. 13 is not different from that in Embodiment 3, aside from the structure for controlling the operation of said electromagnetic solenoid 18, we will omit the explanation herein.

(Operation/effect of the Ophthalmic Microscope)

As a result of the ophthalmic microscope of the present embodiment, it becomes possible to perform the observation of the inspecting eye as follows.

In order to observe an inspecting eye E suffering from common cataracts, the complete coaxis lighting is used. Briefly, it is necessary to set the inclination of the illumination light to be 2°. First, considering the cutout 17 on the filterless closure plate 6 (see FIG. 3A) to be the base position, the control circuit 14 sends a control signal (electric signal) to rotate the stepping motor 11 based on the base position. For example, the control circuit controls the rotation such that the inclination becomes 2° and the corresponding transparent piece 6b3 faces the optical axis of the illumination light. This causes the transparent piece 6b3 to face the beam end 5a of the light guide 5 (see FIG. 4) (S2, S3).

The inclination can be switched by switching the position of each transparent piece without using the cutout 17. In this case, after the examiner or operator performs a pedal operation on the 2° inclination button 13b on the foot pedal 13 shown in FIG. 13, an electric signal is sent to the control circuit 14 to designate the inclination to be 2°. If the current position (rotation angle) of the filterless closure plate 6 is not at the desired angle (herein, the position detection hole 22 indicates the transparent piece 6b3 having 2° inclination), the photo sensor 12 detects the light passing through each position detection hole to control the rotation of the stepping motor 11 such that the transparent piece 6b3 faces the beam end 5a of the light guide 5 when the light passes through the position detection hole 22 (see FIG. 4). Here, similar to Embodiment 2, it is unnecessary to change the correlated color temperature of the illumination light when observing the inspecting eye E. Therefore, the examiner or operator performs a pedal operation on the filterless button 13 on the foot pedal 13 shown in FIG. 13. The filterless button 13c has a characteristic wherein, when the filterless button 13c is ON, the filterless closure plate 6 does not operate in conjunction with the element 6d; however, when the filterless button 13c is OFF, the two components operate in conjunction with each other.

This allows the control circuit 14 to control the electromagnetic solenoid 18 so as to not be introduced to the optical axis of the illumination light L. The element 6d does not operate, and only the transparent piece 6b3 on the filterless closure plate 6 faces the beam end 5a of the light guide 5 (see FIG. 4). The illumination light passing through the transparent piece 6b3 (2° inclination, 3,000K correlated color temperature) is directed by the illumination optics 8 and reflected onto the deflection mirror 9. Thereafter, the illumination light reflected by the deflection mirror 9 and deflected in the parallel direction to the observation optical axis O is refracted by the objective lens 2, and thereby the deflection mirror 9 illuminates the inspecting eye E with (2°) inclination θ1 on the observation optical axis such that the operator or examiner can observe the inspecting eye E.

In addition, this ophthalmic microscope also enables the observation of an inspecting eye E suffering from hypermature cataracts in a similar way. In this case, the correlated color temperature changing filter 6f is used to perform the observation. Different from the observation of the inspecting eye E suffering from common cataracts angle lighting is used in this case. That is, it is necessary to set the inclination of the illumination light to be 6° and the correlated color temperature to be 6000K. Thus, the examiner or operator performs a pedal operation on the 6° inclination button 13e on the foot pedal shown in FIG. 13 to send an electric signal to the control circuit 14 to designate the inclination at 6°. The control circuit 14 sends an electric signal based on the designated 6° inclination to the electromagnetic solenoid 18. First, the control circuit 14 uses the photo sensor 12 to determine the current position (rotation angle) of the filterless closure plate 6 based on the light passing through each position detection hole. When the current position of said filterless closure plate 6 is not the desired angle (herein, the position detection hole 20 indicates the transparent piece 6b1 having 6° inclination), the control circuit 14 controls the rotation of the stepping motor 11 such that, when the light passes through the position detection hole 20, the transparent piece 6b1 faces the beam end 5a of the light guide 5 (see FIG. 4).

At the same time, the electromagnetic solenoid 18 receiving the signal controls the operation such that the element 6d is introduced onto the optical axis of the illumination light L. The transparent piece 6b1 on the filterless closure plate 6 and the correlated color temperature changing filter 6f on the element 6d face the beam end 5a of the light guide 5 (see FIG. 4). Thereby, the illumination light passing through the transparent piece 6b1 and the correlated color temperature changing filter 6f (6° inclination, 6000K correlated color temperature) is directed by the illumination optics 8 to be reflected onto the deflection mirror 9. Then, the illumination light is reflected by the deflection mirror 9. The illumination light deflected in the parallel direction to the observation optical axis O is refracted by the objective lens 2, and thereby the deflection mirror 9 illuminates the inspecting eye E with (6°) inclination θ3 on the observation optical axis O allowing the operator or examiner to observe the inspecting eye E. the illumination optics 8 to be reflected onto the deflection mirror 9. Then, said illumination light is reflected by the deflection mirror 9. The illumination light deflected in the parallel direction to the observation optical axis O is refracted by the objective lens 2, and thereby the deflection mirror 9 illuminates the inspecting eye E with (6°) inclination θ3 on the observation optical axis O allowing the operator or examiner to observe the inspecting eye E.

As mentioned above, in each embodiment, the present invention was explained as an ophthalmic microscope preferable for cataract observation and surgery. The ophthalmic microscope of the present invention can also be readily used for other ophthalmic examinations or surgeries. Accordingly, when using the ophthalmic microscope of the present invention in other ophthalmic examinations or surgeries, it is apparent that the materials and arrangement of the components will be modified, and the inclination favorable to the particular examination or surgery will be employed as appropriate (for example, as shown in FIG. 9, a 4° inclination button 13d is added to the foot pedal 13).

What is claimed is:

1. An ophthalmic microscope comprising: an objective lens placed in front of an inspecting eye;
   a light source for radiating an illumination light;
   illumination optics for directing said illumination light to said inspecting eye via said objective lens;
   observation optics placed along an optical axis of said objective lens;
   a lighting angle switching means placed on the light path of said illumination light to switch the angle of incidence of said illumination light directed on said inspecting eye to the optical axis of said objective lens; and
   a correlated color temperature changing means operating in conjunction with the switching of said angle of incidence by said lighting angle switching means to change the correlated color temperature of said illumination light.

2. An ophthalmic microscope according to claim 1, wherein said light source includes a halogen light, and the switching of the lighting angle to increase said angle of incidence is carried out in conjunction with an operation to raise the correlated color temperature, or the switching of the lighting angle to decrease said angle of incidence is carried out without changing said correlated color temperature.

3. An ophthalmic microscope according to claim 2, wherein said lighting angle switching means comprises a plate member having a transparent piece through which the light of different portions of the beam of said illumination light selectively pass; and a deflection member reflecting the incoming light of different portions of the beam of said illumination light at different positions to direct the light to said inspecting eye via said objective lens.

4. An ophthalmic microscope according claim 3, wherein said lighting angle switching means comprises a first driving means for switching the angle of incidence of said illumination light to the optical axis of said objective lens by driving said plate member to selectively place said transparent piece on the light path of said illumination light; said correlated color temperature changing means including a correlated color temperature changing element comprises a second driving means for selectively placing said correlated color temperature changing element on the light path of said illumination light; and said ophthalmic microscope further comprises a control means for controlling said first driving means in conjunction with said second driving means.

5. An ophthalmic microscope according to claim 4, wherein said plate member includes at least one cutout for detecting the position of said transparent piece.

6. An ophthalmic microscope according to claim 4, wherein said plate member includes at least one detection hole for detecting the position of said transparent piece.

7. An ophthalmic microscope according to claim 3, wherein said illumination light angle switching means comprises said plate member integrated with said correlated color temperature changing means whereby a correlated color temperature changing element for changing the correlated color temperature of said illuminated light is equipped in the transparent piece.

8. An ophthalmic microscope according to claim 7, wherein said lighting angle switching means is constituted so as to be manually operable.

9. An ophthalmic microscope according to claim 7, wherein said lighting angle switching means is equipped with a driving means for driving said plate member so that the transparent piece through which the light of different portions of the beam of the illumination light selectively pass can be selectively moved in and out of the light path of said illumination light and an operating means to direct the selecting operation of said driving means.

10. An ophthalmic microscope according to claim 9, wherein said plate member includes at least one cutout for detecting the position of said transparent piece.

11. An ophthalmic microscope according to claim 9, wherein said plate member includes at least one detection hole for detecting the position of said transparent piece.

12. An ophthalmic microscope according to claim 7, wherein said plate member includes at least one cutout for detecting the position of said transparent piece.

13. An ophthalmic microscope according to claim 7, wherein said plate member includes at least one detection hole for detecting the position of said transparent piece.

14. An ophthalmic microscope according to claim 1, wherein said light source includes a xenon light, the switching of the lighting angle to increase said angle of incidence is carried out without changing the correlated color temperature, or the switching of the lighting angle to decrease said angle of incidence is carried out in conjunction with changing the correlated color temperature to lower said correlated color temperature.

15. An ophthalmic microscope according to claim 14, wherein said lighting angle switching means comprises a plate member having a transparent piece through which the light of different portions of the beam of said illumination light selectively pass; and a deflection member reflecting the incoming light of different portions of the beam of said illumination light at different positions to direct the light to said inspecting eye via said objective lens.

16. An ophthalmic microscope according to claim 15, wherein said illumination light angle switching means comprises said plate member integrated with a said correlated color temperature changing means whereby a correlated color temperature changing element for changing the correlated color temperature of said illuminated light is equipped in the transparent piece.

17. An ophthalmic microscope according to claim 16, wherein said lighting angle switching means is constituted so as to be manually operable.

18. An ophthalmic microscope according to claim 16, wherein said lighting angle switching means is equipped with a driving means for driving said plate member so that the transparent piece through which the light of different portions of the beam of the illumination light selectively pass can be selectively moved in and out of the light path of said illumination light and an operating means to direct the selecting operation of said driving means.

19. An ophthalmic microscope according to claim 18, wherein said plate member includes at least one cutout for detecting the position of said transparent piece.

20. An ophthalmic microscope according to claim 18, wherein said plate member includes at least one detection hole for detecting the position of said transparent piece.

21. An ophthalmic microscope according to claim 16, wherein said plate member includes at least one cutout for detecting the position of said transparent piece.

22. An ophthalmic microscope according to claim 16, wherein said plate member includes at least one detection hole for detecting the position of said transparent piece.

23. An ophthalmic microscope according claim 15, wherein said lighting angle switching means comprises a first driving means for switching the angle of incidence of said illumination light to the optical axis of said objective lens by driving said plate member to selectively place said transparent piece on the light path of said illumination light; said correlated color temperature changing means including a correlated color temperature changing element comprises a second driving means for selectively placing said correlated color temperature changing element on the light path of said illumination light; and said ophthalmic microscope further comprises a control means for controlling said first driving means in conjunction with said second driving means.

24. An ophthalmic microscope according to claim 23, wherein said plate member includes at least one cutout for detecting the position of said transparent piece.

25. An ophthalmic microscope according to claim 23, wherein said plate member includes at least one detection hole for detecting the position of said transparent piece.

* * * * *